United States Patent [19]

Lemelson

[11] Patent Number: 4,671,256

[45] Date of Patent: Jun. 9, 1987

[54] MEDICAL SCANNING, MONITORING AND TREATMENT SYSTEM AND METHOD

[76] Inventor: Jerome H. Lemelson, 85 Rector St., Metuchen, N.J. 08840

[21] Appl. No.: 614,021

[22] Filed: May 25, 1984

Related U.S. Application Data

[63] Continuation-in-part of Ser. No. 614,038, May 25, 1984.

[51] Int. Cl.⁴ .......................... A61K 49/00; A61B 5/05; A61B 6/08; A61N 5/00
[52] U.S. Cl. ...................................... 128/1.1; 128/1.3; 128/654; 128/659; 264/4.1; 264/4.32; 424/1.1; 424/9; 428/402.2
[58] Field of Search ............................ 424/1.1, 9, 22; 428/402.2; 264/4.1, 4.32; 128/1.1, 1.3, 654, 659

[56] References Cited

U.S. PATENT DOCUMENTS

| | | | |
|---|---|---|---|
| 4,209,700 | 6/1980 | Stoddart | 250/363 S |
| 4,310,505 | 1/1982 | Baldeschwieler et al. | 424/1.1 |
| 4,310,506 | 1/1982 | Baldeschwieler et al. | 424/1.1 |
| 4,311,688 | 1/1982 | Burchiel et al. | 424/1.1 |
| 4,323,546 | 4/1982 | Crockford et al. | 424/1.1 |
| 4,331,647 | 5/1982 | Goldenberg | 424/1.1 |
| 4,334,017 | 6/1982 | Plotkin | 435/7 |
| 4,348,376 | 9/1982 | Goldenberg | 424/1.1 |
| 4,361,544 | 11/1982 | Goldenberg | 424/1.1 |
| 4,429,008 | 1/1984 | Martin et al. | 424/1.1 |
| 4,444,744 | 4/1984 | Goldenberg | 424/1.1 |
| 4,448,765 | 5/1984 | Ash et al. | 424/1.1 |
| 4,460,559 | 7/1984 | Goldbenberg | 424/1.1 |
| 4,460,560 | 7/1984 | Tölkes et al. | 424/1.1 |
| 4,460,561 | 7/1984 | Goldenberg | 424/1.1 |
| 4,466,951 | 8/1984 | Pittman | 424/1.1 |

Primary Examiner—Christine M. Nucker

[57] ABSTRACT

A system and method for detecting, monitoring and treating a malady such as a disease in a living being. In one form, a dose of a drug formed of a multitude of drug units containing antibodies and a nuclide or nuclides is administered to a living being having one or more disease sites, such as malignant tumors or other forms of malignancy wherein the antibodies target the units to antigens at the disease site. Such targeting concentration of drug units is detected by scanning radiation generated either by radioactive nuclides tagged to the drug units or by activating normally inactive nuclide material in the drug units with radiation such as neutrons generated externally of the living being and directed through the body. The results obtained are employed to control the positioning and operation of one or more neutron beam generators for controllably directing a beam of neutrons through the body to the disease site to activate nuclide material targeted thereat and cause same to generate local cell killing radiation such as high velocity particles of reaction. Detection and monitoring of radiation generated when miniature nuclear explosions occur locally is automatically effected to determine the effect and results of such treatment. If required, one or more repeated administrations of the drug and its activation at the site or sites of the disease are effected, preferably under computer control. The system and method also provide for the detection and monitoring of malignancies and the like by means of X-rays or other form of radiation passed through the body of the patient being treated.

39 Claims, 8 Drawing Figures

FIG. 1.

MEDICAL SCANNING, MONITORING AND TREATMENT SYSTEM AND METHOD

RELATED APPLICATIONS

This is a continuation-in-part of copending application Ser. No. 614,038 filed May 25, 1984 for "Compositions of Matter for Use in Medical Treatment".

SUMMARY OF THE INVENTION

This invention relates to a system and method for diagnosing, treating and monitoring a disease, such as cancer with radiation which is selectively generated at the site of a malignancy or tumor, such as immediately adjacent to and within the tumor wherein the treatment radiation is generated in a manner to minimize or eliminate damaging effects on normal tissue adjacent the tumor(s). In particular, the invention is concerned with an electronic system and electromechanical apparatus controlled thereby for detecting, monitoring and treating diseases with disease killing radiation which is specifically applied to diseased tissue without the need to pass such radiation through and detrimentally affect or destroy normal tissue existing between the diseased tissue and the exterior of the body, a condition which frequently occurs during conventional radiation therapy.

In the treatment of certain diseases, such as cancer, cell-killing radiation has been employed which is generally generated externally of the patient and is passed through normal tissue to intersect an internal malignancy or tumor or cell-killing radiation generated by a small quantity of a radiation emitting material such as radioactive cobalt implanted in or adjacent a tumor has also been employed. The technique has a number of disadvantages including the requirement to provide an incision or otherwise pass the radioactive material through normal tissue which it may damage, and may have a damaging effect on normal tissue adjacent the tumor in or adjacent which it is disposed.

The instant invention employs units of a drug which contain one or more small quantities of a nuclide or a plurality of nuclides, as disclosed in my copending patent application entitled "Compositions of Matter for Use in Medical Treatment", which drug units are caused to become concentrated at the site or sites of tumors, malignancies or other forms of diseased tissue or antigenic material to which such drug units are targeted by antibodies forming part of such units. While one of the nuclides of the drug units may comprise a radionuclide which is normally radioactive and generates a low level of detectable radiation for detecting and monitoring the location or locations of concentrations of the drug units at the diseased site or sites, the other nuclide which forms part of the same drug units is normally inactive or not radioactive and may be rendered destructively radioactive or atomically explosive by means of radiation, such as neutrons generated outside the body being treated wherein the nuclear reactions which occur may be controllably limited to reduce or eliminate the damage to normal body tissue normally experienced with conventional radiation treatment. The radiation generated during the atomic disintegration or transformation of such nuclide may also be used for monitoring its intensity and distribution and the results or effects thereof on the diseased tissue or tumor. A nuclide which is not normally not radioactive but is capable of being rendered radioactive with externally generated radiation may replace or supplement the radionuclide in the drug units, and used to generate detectable radiation for detection and monitoring purposes prior to and/or after treatment with nuclide material of the drug units which, upon being so rendered radioactive, generates higher intensity radiation capable of effecting treatment such as by destroying cancer cells in the immediate vicinity of the drug units at the site of the cancer.

The apparatus of the instant invention includes means for scanning the body or a portion of the body of a living patient either with externally generated radiation, such as X-rays, ultrasonic wave energy or other form of radiation or by means of internally generated radiation such a nuclear magnetic resonance radiation generated by an external magnetic field which radiation is employed to effect either the generation of a direct image or a computerized axial tomographic image on a display screen such as the screen of a cathode ray tube (CRT). The information contained in such image or images so generated is utilized to determine the location and extent of the diseased or cancerous tissue or tumor(s) either by human monitoring and/or by computerized image analysis. Such information is then use to manually or automatically control one or more motors to properly locate and direct one or more beams of radiation, such as neutrons, which radiation is operable to activate and cause units of nuclide material, such as boron-10 to become radioactive in a manner to generate and effect localized miniature atomic reactions or explosions which are effective in destroying local cancer cells disposed adjacent to or surrounding the drug units targeted to the antigenic material of the cancer cells. The system and method also includes means for automatically administering additional doses of drug units for effecting further monitoring and treatment of the disease or tumor cells.

Accordingly it is a primary object of this invention to provide a new and improved system and method for detecting, monitoring and treating diseases, such as cancer, existing within a living being.

Another object is to provide an improved apparatus and method for effecting radiation treatment of a tumor, such as a malignancy, wherein the radiation is generated for a limited period of time at the site of the tumor.

Another object is to provide an improved system and method for treating a malady such as a tumor or malignancy located within a living being wherein such treatment includes radiation for destroying cells of the tumor which radiation destroys substantially only the cells of the tumor.

Another object is to provide an improved method for generating radiation for detecting and treating cancer with localized radiation generated when a small quantity of a nuclide is activated within a living being by externally generated radiation passed through the body which radiation does not have a cell destroying effect.

Another object is to provide an improved method of treating disease such as a malignancy, which is localized within a living being employing antibodies, such as monoclonal antibodies to deliver small quantities of radiation generating drugs directly to the site of and within the diseased tissue or malignancy.

Another object is to provide an apparatus and method for treating and destroying tumors including malignant growths within a living being with miniature atomic explosions generated within such tumors by the proper application of radiation to nuclide material delivered to the tumors wherein such activating radiation is timed and directed under computer control.

Another object is to provide a new and improved apparatus and method for effecting the total destruction of tumors located within a living being.

Another object is to provide a new and improved method for monitoring the treatment of diseased tissue, such as tumors.

Another object is to provide an apparatus and method for simultaneously treating or destroying a tumor or malignancy and monitoring the effects of such treatment.

Another object is to provide a method for treating a tumor or malignancy by incrementally physically destroying the cells thereof with explosive radiation.

Another object is to provide a system and method for monitoring internal abnormal growths, such as malignancies, by generating images of such abnormal growths with radiation which is generated within the growths and is detected to provide images of such growths.

Another object is to provide improvements in apparatus employed to detect and locate tumors and the like existing within a living being and to treat or destroy such tumors with radiation generated at the site of the tumors.

Another object is to provide an improved method for destroying tumors and malignancies in a living being under the control of a computer which operates to optimize the treatment by controlling the amount and direction of treatment radiation.

Another object is to provide an computer controlled system for treating disease such as cancer within a living being wherein signals derived from one or more detectors detecting radiation which passes through or from the site of the disease are automatically analyzed and the information derived from such analysis is employed to optimize such treatment.

Another object is to provide improvements in an apparatus for monitoring and treating tumors and the like.

Another object is to provide a method and apparatus for sequentially locating and treating tumors which exist within a living being in a manner such that the treatment is optimized.

Another object is to provide a new method for generating pictorial information, such as images, of internal organs, tumors and the like existing within a living being by means of radiation which is controllably generated within the living being for a short period of time, thereby reducing the effects of such radiation on normal tissue.

Another object is to provide a new and improved method for detecting tumors and the like growing within a living being by means of radiation which is generated at the site of the tumor or tumors but not generated when the source thereof, a nuclide, is administered to the living being, thereby eliminating the effects of such radiation of tissue and cells past which such nuclide flows in reaching the site at which detection is effected.

Another object is provide improved methods for delivering and dispensing drugs at the site of treatment therewith.

Another object is to provide a system and method for controlling the release of drugs within a living being for effecting controlled treatment of a disease or tumor.

Another object is provide an apparatus and method for controlling the generation of radiation deep within a living being to permit such radiation to treat various maladies existing within such living being.

Another object is to provide an apparatus and method for automatically treating a human malady or disease such as cancer wherein a computer is employed to effect the detection and location of the site or sites of the disease and the administration and activation of drug units which partake in the automatic treatment so as to optimize or properly control such treatment.

With the above and such other objects in view as may herein more fully appear, the invention consists of the novel apparatus and methods for detecting and treating maladies as more fully described herein, but it is to be understood that changes, variations and modifications may be resorted to which fall within the scope of the invention as claimed without departing from the nature and spirit of the invention.

DESCRIPTION OF THE DRAWINGS

Detailed Disclosure

In the drawings.

Figure 1:
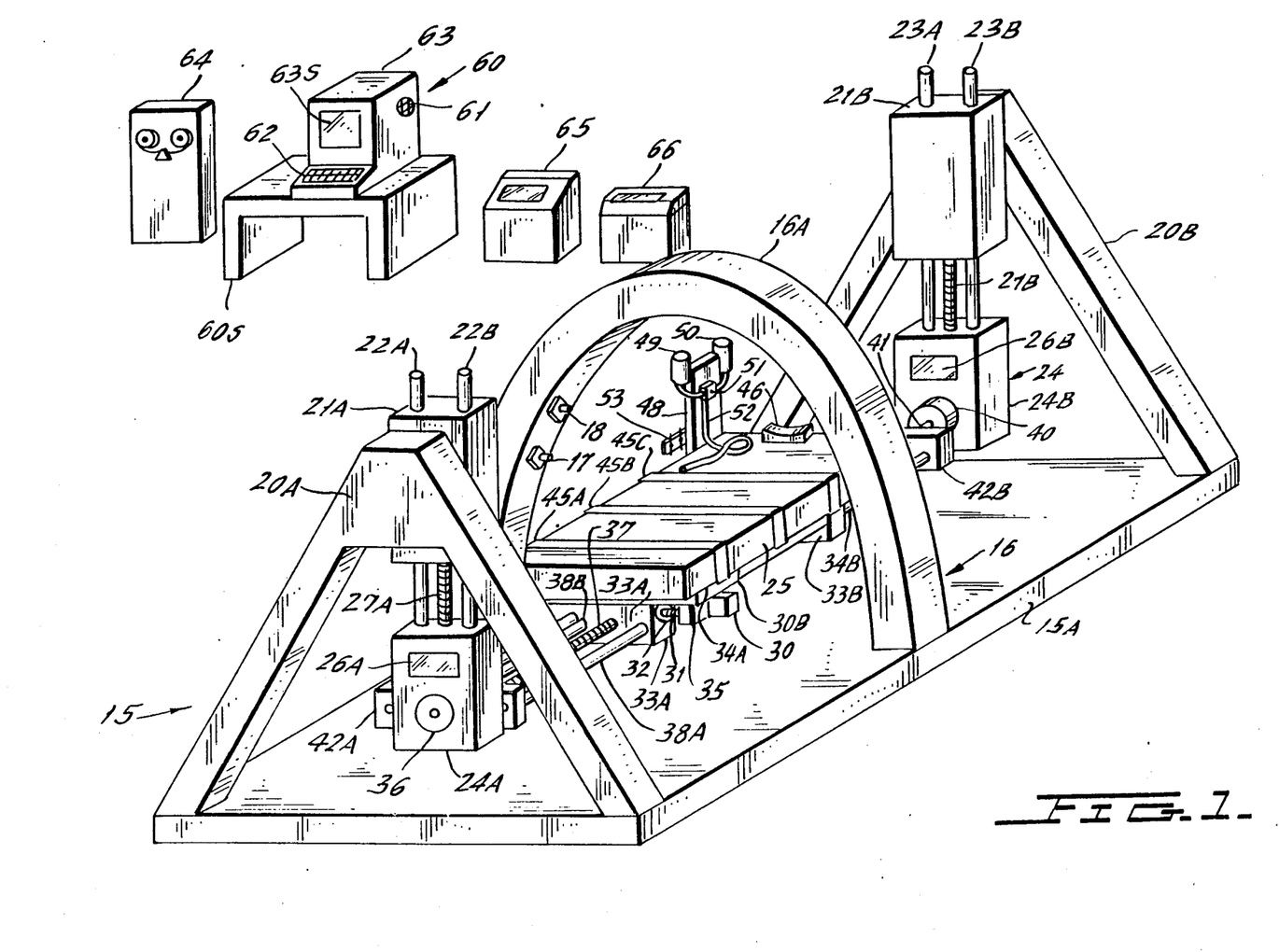
FIG. 1 is an isometric view of components and subsystems of a medical detection, monitoring, disgnosing and treatment system for human beings including patient scanning and monitoring apparatus, a computer for controlling such scanning apparatus, a video display, a character printer and a graphics printer.

In FIG. 1 is shown broad details of the components and subsystems of a computerized scanning and control system for the radiation treatment of living matter, such as a living human being such as in the treatment of various diseases.

A first assembly 15 includes a platform, mount or base 15A which supports an upstanding arcuately shaped frame or rail 16 defining a rigid support and housing 16A containing a plurality of sensor-emitters 17, 18. Such frame 16 is shown supporting one or more transducing assemblies, each containing one or more radiation detectors 17 and radiation emitters 18 which will be described in greater detail. Also supported by platform 15 is a support table or couch 25 and end frames or supports in the shapes of A-frames 20A and 20B. Supported by the end A-frames 20A and 20B are respective couch support blocks 21A and 21B, each containing respective pairs of vertically aligned slide bearings for slidably supporting respective pairs of vertically extending cylindrical shafts denoted 22A, 22B and 23A, 23B, each of which pair of shafts supports a respective solid block 24, denoted 24A and 24B at their ends, between which blocks extend a pair of parallel shafts 38A, 38B supporting the couch 25. The assembly of the couch 25, shafts 38, end blocks 24 and vertical shafts 22 and 23, is thus supported for z-axis vertical guided movement by blocks 21A and 21B. Z-axis powered adjustment of the vertical position of the couch 25 is effected by the controlled operation of a pair of motors 26A and 26B, which may be signal controllable reversible gear-motors or stepping motors which are respectively supported by the blocks 24A and 24B. Said motors rotate lead screws 27A and 27B causing such lead screws to advance or retract the shafts in threaded holes centrally disposed in respective of the support blocks 21A and 21B.

X-axis controlled positioning of the table or couch 25 is effected by the controlled operation of a reversible stepping or feedback signal controlled gear-motor 30 which is supported by a block 30B which supports and guides table 25 in movement laterally across and above lower platform 15. Motor 30 is coupled to rotate its lead screw 31 about an X-axis causing such screw to advance or retract through a threaded bearing 32 in a base support block 33A. A base support 34A for the couch 25 is attached to a support plate 35 for motor 30. Such support 34A is also attached to block 33A by sliding guides (not shown) permitting smooth X-axis motion thereof. A similar base support 34B is also shown in part and such support is attached to support block 33B by similar X-axis sliding guides to permit suitable X-axis adjustment of the position of the couch or table 25.

Y-axis motion of the couch 25 is effected by the controlled operation of a reversible stepping or feedback signal controlled gear-motor 36 which is supported by a block 24A, which motor rotates a Y-axis lead screw 37 causing said screw to advance or reverse travel with respect to the bearing guide defined by a threaded bore in blocks 33A & 33B for effecting Y-axis movement of the couch. Smooth linear Y-axis adjustment is ensured by supporting blocks 33A and 33B on sliding guiderails 38A and 38B.

Controlled rotation of table 25 is effected by the controlled actuation of a geared stepping motor or a rotational position feedback controlled motor 40 supported by block 24B. Controlled operation of a gear motor 40 effects the controlled rotation of a shaft 41, which in turn causes end supports 42A,42B affixed to the rails 38A and 38B to rotate, causing the entire couch assembly supported by such rails to rotate about a horizontal axis. Also provided attached to the couch 25 are a plurality of patient restraint straps 45A, 45B and 45C and a headrest 46. Such straps and headrest are employed to maintain the patient in a fixed position on the couch 25 as the couch moves during a monitoring and/or treatment cycle. The upper surface of the couch 25 may also be provided with lines or grid marks and numerical indicia for use in properly positioning and repositioning a patient thereon and in analyzing the results of scanning and treating such patient in the manner which will be described hereafter.

Also illustrated in FIG. 1 is an intravenous drug dispensor stand 48 which is supported above the base 15 by suitable means. Supported by stand 48 are a plurality of reservoirs, such as removable bottles 49 and 50 for containing a plurality of different drugs to be administered to the patient during monitoring or disease detection and/or during the treatment thereof in the manner to be described. The administration of such drugs may be effected in an automatic manner by means of respective solenoid control valves or motors which are automatically controlled to operate pumps or valves in a manner to regulate and control the flow rate of liquids from such reservoirs. Notation 51 refers to a control switch and 52 to an intravenous injection flow tube which will be described. Also supported by stand 48 is an intravenous needle rack 53 for the storage of such auxiliary needles and intravennous injection accessories as are necessary to properly effect the monitoring and treatment of disease of a patient disposed on the couch 25.

Also shown in FIG. 1 are units including housings containing electronic controls and interface equipment for the proper operation of the computerized scanning and control system. A stand 60S supports a housing 60 containing an assembly 60A which contains a computer and an electronic control system 10 for controlling the operation of the computerized scanning and control system. Such stand also supports a speaker 61, a user accessible keyboard 62 and a video display 63 having a monitor screen 63S which may be used to display command and control information, to display monitorable data including digital data and graphical or reconstructed image data to permit the real time observation of internal tissue and organs of a patient as well as data generated in the past so as to permit the review of previously recorded data derived from scanning signals output by sensors employed and image information derived therefrom. A mass storage device 64, is provided which may comprise an erasible magnetic disc or tape recorder-reproducing unit, such as a floppy or hard disc storage system or other form of rapid access archival mass storage means. Additional peripheral equipment includes a line printer 65 and a graphics plotter 66 which may be used to provide respective forms of hard copy defined by signals output by the computer or computers employed in the system and by signals generated by the detectors employed. While the computerized scanning and control system for radiation treatment is shown as an assembly of separate functional components or modules, an integrated construction may be employed in which all of such described equipment is supported by the base 15, preferably in a single housing or group of housings which are adjacent each other.

Figure 2:
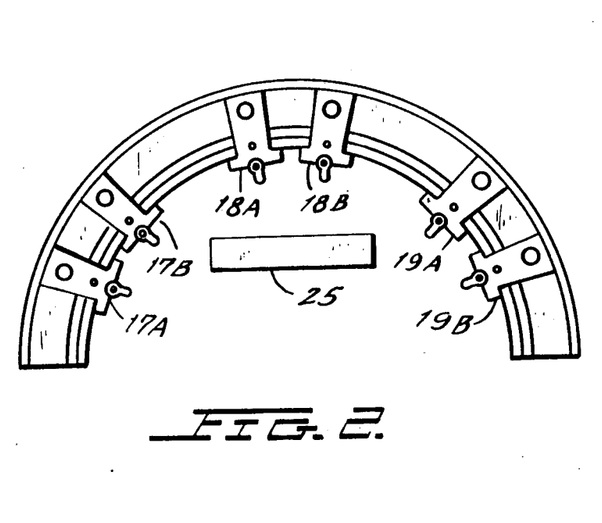
FIG. 2 is an end view with parts removed for clarity of an arcuately shaped mount for a plurality of radiation beam emitters and sensos forming part of the apparatus of FIG. 1.

In FIG. 2 is shown details of the internal construction of the support 16 for a plurality of radiation sensors and, if employed, emitters mounted on the arcuate support 16. A plurality of radiation detectors 17A and 17B and a plurality of neutron beam sources 18A and 18B and X-ray emitters 19A and 19B form part of the system. All detectors/emitters are supported below the upper portion of arcuate track 16B which defines the main support for frame 16. Each detector-emitter contains a reversible gear motor and may thus be driven to any position on the gantry 16 by utilizing a toothed track 70 which is affixed to the arcuate track or gantry 16T.

While but two adjacently located sensor/emitters of each type are illustrated and are used within the current embodiment, the system may comprise an additional number of such sensor/emitters capable of being positioned or driven to any select locations along the track of the gantry 16. A large number of sensor/emitters will allow faster and, in certain instances, more highly resolved operation of the system and may be utilized where such higher resolution and faster operation are requisite or desired.

Figure 3:
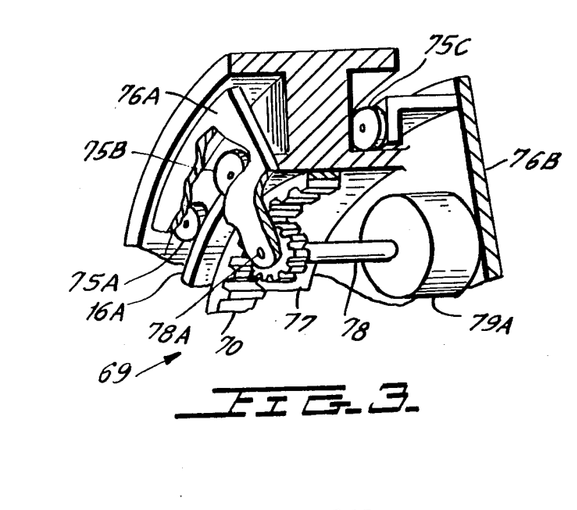
FIG. 3 is a partical isometric view with parts sectioned and broken away for clarity of a mounting arrangement for the positionable sensors and/or emitters of FIG. 2.

In FIG. 3 is shown a typicl mounting arrangement 69 for a typical sensor/emitter pair on the gantry track 16T. A plurality of pairs of wheels 75A/75B supported on respective sensor support face plates 76A and 76B permit rolling movement along the inner surface 16S of the I-cross section shaped gantry track 16T. Tension is maintained between such wheels and the inner surface 16A by a drive gear 77 supported by the face plate 76 on a shaft 78 extending through a bearing 78A and a gantry supported track gear 70. Circumferential positioning of the sensor support assembly on the gantry 16 is accomplished by the actuation of a geared stepping motor or a shaft position/rotation encoded motor 79 which is supported on face plate 76B.

Figure 4:
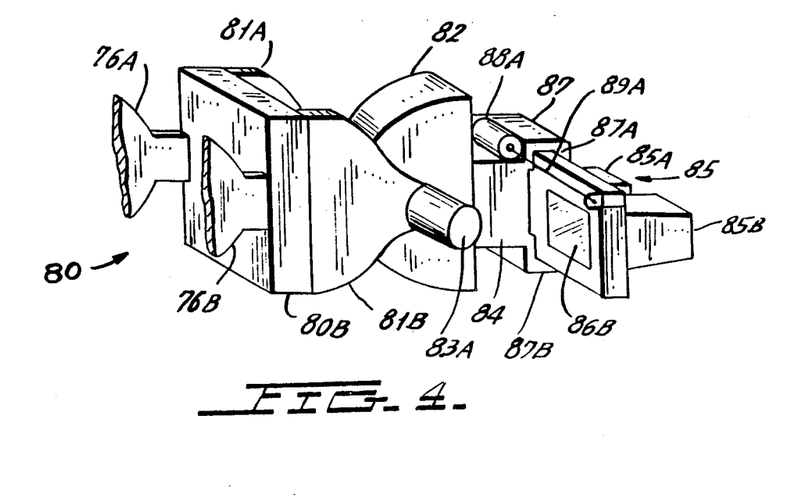
FIG. 4 is an isometric view with parts broken away for clarity of the support assembly for the sensors and/or emitters of FIG. 2.

FIG. 4 illustrates further details of the construction of an emitter/detector support assembly 80. Attached to and supported by face plates 76A and 76B is a base 80B for rotationally supporting the sensor assembly, from which base extends a pair of pivotted supports 81A and 81B. A sensor base counterweight 82 is shown supported by a rotatable axle which passes through the center of gravity of counterweight 82 and is driven in rotation by a reversible feedback controlled or stepping motor 83. Such rotation effects controlled angular positioning of the affixed sensors within the plane of the gantry track.

The radiation sensor may comprise a scintillation counter and/or a television camera or the like. In the form illustrated, a light proof housing 84 contains a photomultiplier tube or its equivalent and associated optics as in FIG. 5. In FIG. 4, the radiation to be detected travels from right to left and enters a radiation collimator 85 and passes therethrough to a suitable scintillation or phosphorescent screen 86A. The secondary light emission from such screen is detected by the photomultiplier. A single photomultiplier and positioning assembly may be employed to detect either or both X-ray and gamma radiation by means of appropriate collimator design and material and the use of a secondary emission screen. A single assembly is shown constructed with a gamma ray collimator 85B and scintillation screen 86B affixed parallel to an X-ray collimator 85A and secondary emission detection screen 86A which assembly may be shifted laterally with respect to tracks 87A and 87B of a guide 87 to position the collimator/screen assembly along the optical axis of the photomultiplier. Such lateral assembly shift is accomplished through a force transmission rod 89A by the actuation of a solenoid or motor 88A.

Figure 5:
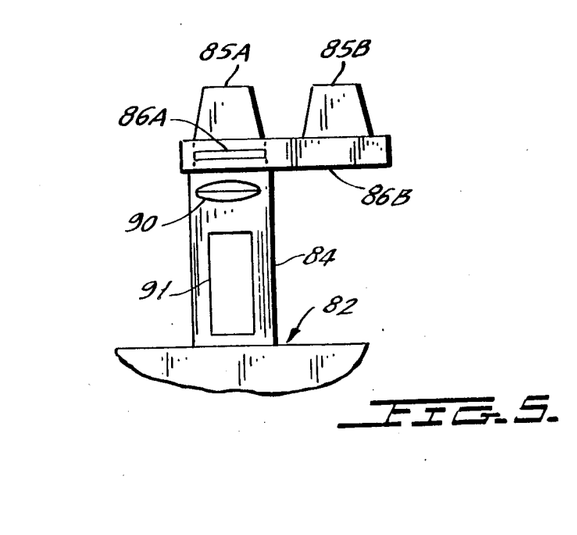
FIG. 5 is an end view showing details of a typical sensor assembly of the type shown in FIG. 2.

FIG. 5 shows details of the detector assembly. A focusing lens 90 collects the light from the detector screen 86A and focuses it on the photocathode of a photomultiplier tube 91 for detection.

Figures 6, 7:
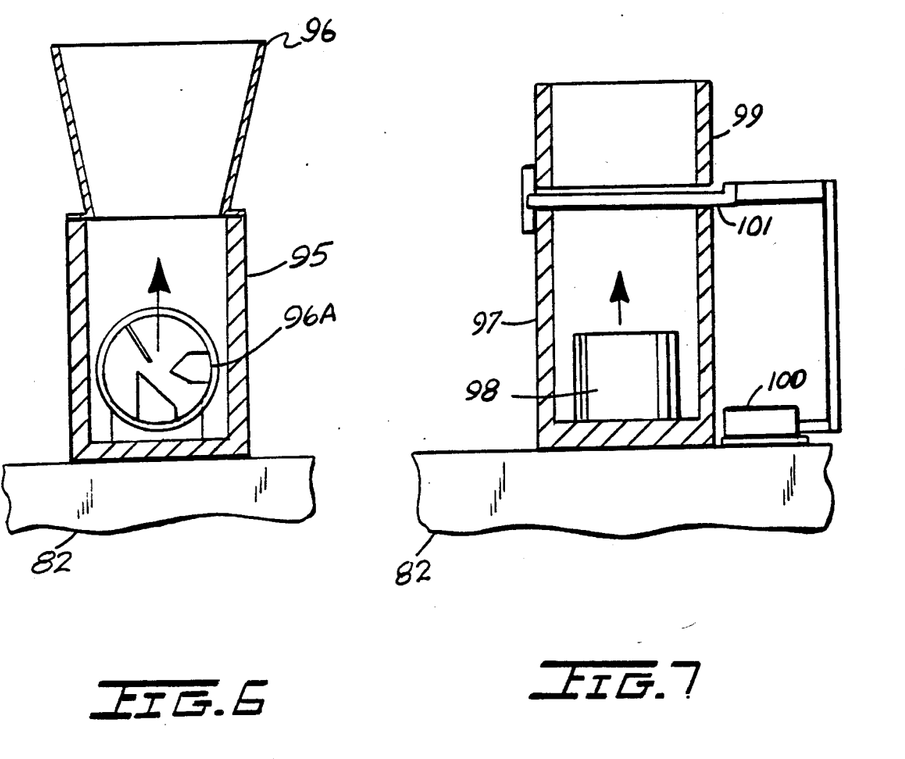
FIG. 6 is an end view with parts broken away for clarity of an X-ray emission means and assembly therefore applicable to the apparatus shown in FIGS. 1 and 2.
FIG. 7 is an end view with parts sectioned for clarity of a source of neutron beam radiation and its mechanical gating means applicable as an radiation emitter for use with the apparatus of FIGS. 1 and 2.

FIG. 6 shows details of the construction of an X-ray projection source which may be employed, as described, in the computerized scanning and control system. A radiation shielding cannister 95 contains an X-ray tube 96A. Also supported by the cannister 95 is an X-ray modulator and dispenser 96, which produces a fan-shaped exit beam of uniform intensity and known angular divergence in a two dimensional plane.

In FIG. 7 is shown a construction similar to FIG. 6 wherein a source of neutrons replaces the X-ray source. Enclosed in an open ended housing 97 is a neutron-neutron source material 98. Supported by housing 97 is a neutron collimator 99 which only allows well collimated neutrons to exit therefrom along a pointing or directed axis. Neutron flow intensity is controlled by the actuation of a solenoid 100 which slides a shutter 101 constructed to block neutrons from the source, into and out of the path of the neutrons.

Figure 8:
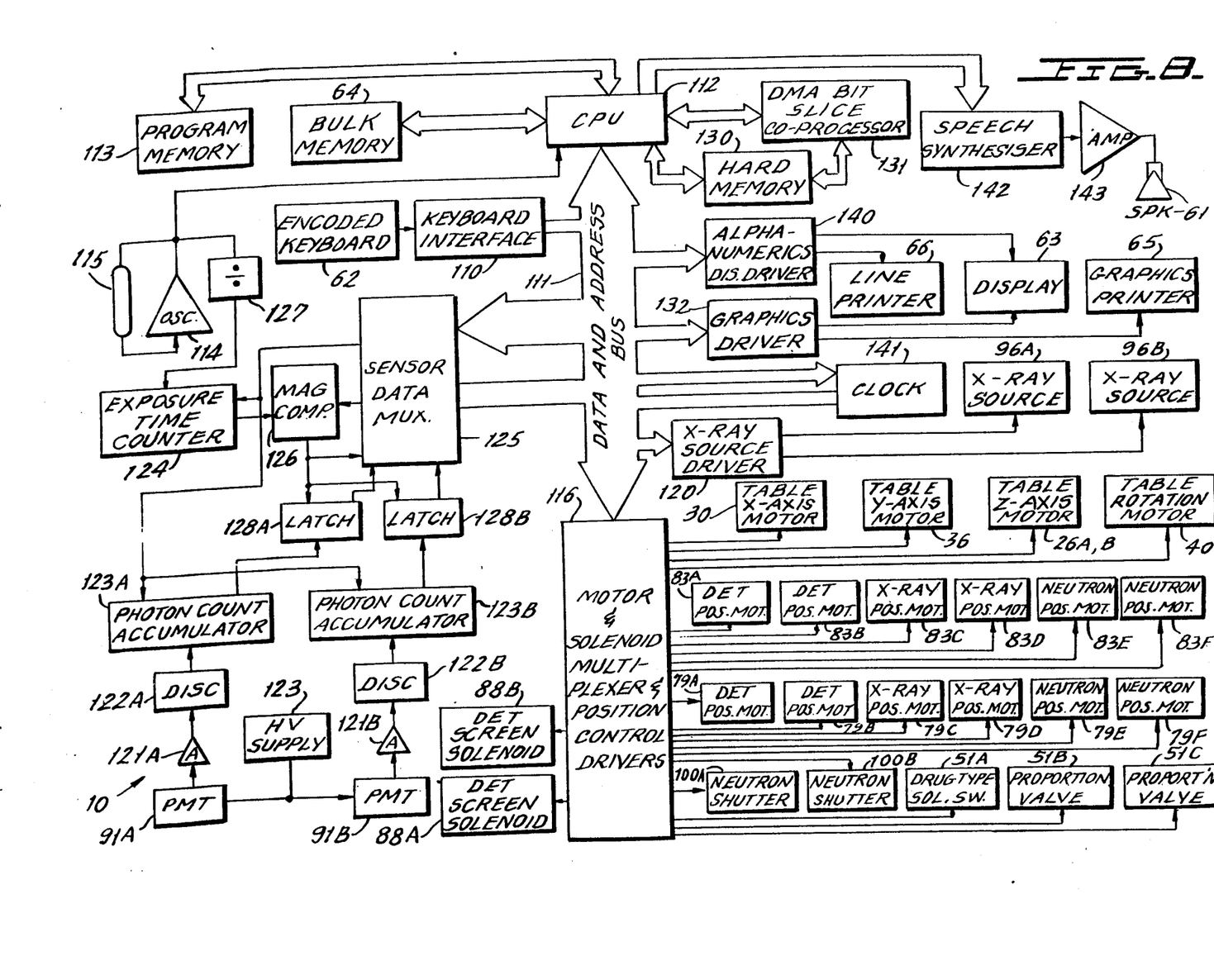
FIG. 8 is a schematic diagram illustrating an electronic control system and subsystem components of the medical monitoring, scanning and treatment system illustrated broadly in FIG. 1.

FIG. 8 shows details of the electronic control system for the computerized scanning and control system for radiation treatment. Such system 10 may be manually addressed or controlled by an operator who enters system commands as are necessary by the selective operation of the keys of keyboard 62. Such input instructions are transferred via a keyboard interface 110 and a system bus 111 to a central processing unit 112 of a digital computer wherein they are electronically processed according to the instructions recorded in a program memory 113. Central processing unit timing and synchronization are accomplished by means of a frequency stable oscillator 114, having suitable feedback means such as a crystal 115, the output signals of which oscillator are employed for such synchronization.

Cycle starting may commence after a patient is positioned on the couch or table 25 on which such patient is predeterminately located and retained by strapping so that the body or portion of the patient desired to be monitored and treated, is within the plane of the sensor mounted gantry housing 16. Positioning information is derived from signals entered by the selective operation of the keys of the keyboard 62 or is reproduced from previously recorded coordinate signals provided in mass memory 64. Parameters relating to the desired positioning of the patient couch or table 25 at a selected X, Y and Z coordinate location with respect to the base and a selected tilt or rotational position with respect to its longitudinal axis is effected by means of signals generated from the central processing unit 112 and transmitted on bus 111 through multiplexers 116 for the respective motors and solenoids, wherein the position command codes derived are interpreted as proportional electrical signals which are applied to control the X-axis motor 30, the Y-axis motor 36 and the Z-axis motors 26A and 26B as well as the table rotating motor 40. The motor multiplexer and driver 116 are not detailed as such devices are well known in the art and generally contain address and data decoders and device drivers or stepping motors for effecting the desired movements.

Once the patient has been predeterminately positioned, the functional operation of the system in monitoring and/or radiation treating the patient may be initiated. A computer axial tomography scan may be initiated by computer or manually controlled positioning of the X-ray sources 96A and 96B by means of signal control of the X-ray source position motors 79C and 79D and the tilt position motors 83C and 83D resulting from signals generated by the central processing unit 112 and transmitted on bus 111 to the motor multiplexer and control drivers 116. Signals transferred from the central processing unit (CPU) 112 on bus 111 also comprise data which is employed to control the operation of motors 79A, 79B and 83A, 83B which respectively position the photomultipliers 91A and 91B along the track of the gantry and effect predetermined tilting or rotation of the photomultipliers on their mounts to properly aim same to detect radiation generated within or passed through the patient. When all select or predetermined patient source and detector positioning commands have been generated and applied and, when the X-ray sensitive detector screens 85A and 85B have been selected by the proper actuation of screen solenoids 88A and 88B in response to instructions received from the CPU 112 which are transferred via bus 111 and the solenoid multiplexer and driver 116 are activated, a computerized axial tomography (CAT) scan may begin.

The X-ray sources 96A and 96B are generated at intensities defined by data incorporated in signals received from the CPU 112, which signals are transferred via bus 112 to X-ray source driver 120. X-ray source patterns are predeterminately selected so as to be appropriate for effecting fan projection tomography (FPT).

The X-radiation detectors are operated in a photon counting mode as follows: X-rays which are transmitted through the patient's body are attenuated differently along different rays of the fan projection according to variations in the internal structure density of the patient. Since each of the optic axes of the photomultipliers 91A and 91B point along different rays emerging from sources 96A and/or 96B which have been attenuated by the patient's body, the phosphorescent screen in front of each detector (91A and 91B) will emit radiation and glow according to the intensity of the transmitted X-rays and such light creates proportional photon pulse signals from the anodes of each detector when an appropriate high voltage supply 123 is connected to the dynode chain of each photomultiplier tube. Such pulse signals are amplified in amplifiers 121A and 121B and are conditioned by pulse discriminators 122A and 122B. The pulse output of each discriminator 122A and 122B is counted and accumulated in the photon counters 123A and 123B. At the time the X-ray intensity measurement starts, the CPU generates and sends a reset signal to the exposure time counter 124 via bus 111 and sensor data multiplexer 125 while simultaneously loading a count number which is proportional to the desired exposure time into a magnitude comparator 126. When the count of clock pulses generated by oscillator 114 and passed through a divider 127 to a counter 124 attains the preset count applied to the input of the magnitude comparator 126, the output of comparator 126 receives a true value which sets a plurality of photon data count latches 128A and 128B to the current photon count intensities set in such counters. The signal output by the comparator 126 also causes a bus interruption to the CPU 112 which allows the CPU to reset counter 124 and the photon counters 128A and 128B through bus 111 and multiplexer 125 and also transfers the count outputs of latches 128A and 128B to a memory 130 (via MUX 125 and bus 111) for further processing.

A full computerized axial tomography scan function may consist of many intensity readings derived when the detectors are positioned at slightly different locations as previously described, for each CAT scan but with the optic axis of the detector unchanged and located along a ray axis of the source. Two detectors are shown, in order to simplify the drawings, but additional detectors may be provided to permit additional rays to be sampled for each scan or shot, thus decreasing the scan time and the total patient X-ray dose. If such additional detectors are employed, they preferably are located to use equiangular spacings to facilitate their implementation in the described fan-projection mode. Analysis and reconstruction of the tomographic image may also be accomplished in real time, independent of the concurrent operation of the CPU 112, from the signals derived from X-ray sampling by means of a fast co-processor 131, such as a bit slice processor, having hardware multiplication implementation, which also has direct memory access capabilities. Once image reconstruction has been accomplished, such as by implementation of the Fourier slice theorem algorithms which are well known in the art, the reconstructed image may be placed at a select location in a memory 130 for later access and use by the CPU 112.

Immediately display of the computer reconstructed image may be accomplished by instructing the central processing unit 112 to transfer the image data recorded in memory 130 to a graphics driver 132 wherein representative analog video signals are generated which are conducted therefrom to display monitor 63. Alternatively, graphics driver 132 may be operable to convert and transfer such image information to a graphics or film printer 65 to provide hard copy of such image information.

The image information stored in memory 130 may be used for the detection and location of a malignant or nonmalignant tumor or otherwise diseased internal body organ or bone. The system may thus be further used both for the detection and analysis and treatment of tumors and the like. In such a detection mode, the coordinates and density of the tumor and the surrounding body tissue may be calculated based on the results of analyzing the image information derived from one or more computerized axial tomography scans or scanning sweeps. Such derived information, including information for assisting or guiding an operator of the equipment, if so operated, may be used to administer suitable chemical or radiation generating drugs to the body of the patient from such reservoirs under the control of respective proportioning valves 51B, 51C, etc. controlled by signals generated by CPU 112 in accordance with computer processing the image information and instructions received from program memory 113, as well as comparisons with past data stored in memory 64. Such control or actuation signals are passed from the CPU 112 via bus 111 and MUX and driver 116 to the drug delivery controls 51A, 51B and 51C for effecting control of the delivery of the one or more drugs controlled thereby.

Further CAT scans may be taken concurrently with the administration of the drug or drug units described or at one or more calculated or predetermined times after such drug or drug units are administered. For the delayed administration of the drug or drugs, the system positioning parameters and image data are transferred to the bulk memory 64 via CPU 112 for later reference.

An alternative automatic control means is provided for adaptive radiation therapy. Such mode of operation is similar to the mode defining the step set forth above. The drugs administered in this mode are either radionuclides which generate a low level of detectable radiation or nuclides, such as boron 10, which become radioactive when receiving and absorbing radiation such as neutrons. The drug units containing such nuclide or nuclides travel through the body via the bloodstream. After the elapse of sufficient time for the drug units to be targeted by means of their antibodies to disposed the nuclide or nuclides adjacent specific antigens, such as existing at or within one or more tumors or adnormal growths or in infected tissue, system 10 may be automatically operated to predeterminately steer and position one or more collimated neutron sources using the tumor position information derived from the described CAT scan, or a CAT scan employing detectors or radiation generated by the nuclide units when activated with externally generated neutron radiation or the like. Such detector and emitter positioning is accomplished by means of commond control position signals generated by the CPU 112 which are applied to driver 116 to the neutron source positioning motors 79E and 79F and the neutron source tilt motors 83E and 83F. Once so predeterminately positioned, exposure of the cells of the tumor to the destructive effects of radiation or particles generated by the neutron activated nuclide particles of the combined drug units at the tumor site is effected in a controlled manner by signals reproduced from the CPU 112, which signals control actuation of the respective neutron source shutter solenoids 100A and 100B. Progress attained in effecting tumor destruction and information relates to the in situ radiation generated, may be monitored as follows. The radiation detectors are switched to their gamma-ray sensitive operating mode by signals generated by the CPU 112 by the actuation of a pair of detector screen solenoids 88A and 88B via bus 111 and MUX solenoid driver 116. An emission tomography scan may then be accomplished in the same manner employed in effecting the previous CAT scan but without the use of the X-ray source, since the activated nuclides, which are carried by the drug units adjacent the tumor site and/or within the tumor, provide sufficient radiation to effect imageing per se or tumor destroying radiation containing suitable image radiation. The results of the neutron bombardment of the tumor site and the units of nuclide thereat may thus be monitored continously by effecting the adaptive control of the positioning of the source of neutron, their intensity and direction through the body along a select path or paths or controlled scanning path movement with respect to the tumor site so as to predeterminately provide radiation for monitoring and treating or destroying cells of the tumor in accordance with the information derived from such monitoring and the controlling administration of the nuclide containing units to the body as described.

A further modification of such method allows the system to operate in a manner similar to that previously employed in effective adaptive radiation therapy in which the nuclide does not itself become radioactive but undergoes a local chemical change under the influence of an applied neutron flux. In this mode of operation, CAT scans may be effected by repeated X-ray projection tomography in order to monitor and check on the progress of the therapy. Otherwise operation of the system may be identical to that which is previously described.

Additional functions of the system, as indicated in FIG. 8, may comprise the display of alpha-numeric command-control and data information on the monitor 63 in accordance with signals transmitted thereto from the CPU 112 to an alpha-numeric display driver 140 which converts such signal to video signals for properly controlling the display writing means. Alternatively, such command control signals and data signals may be appropriately converted and transferred from the driver 140 to the line printer 63 for producing hard copy thereof.

A system clock 141 is included to permit data and time information to be automatically recorded along with other pertinent patient data, CAT scans and treatment progress by the printer 63 or to be displayed on the display screen.

To further facilitate the operation of the system, a speech synthesizer 142 is provided which is addressable by the CPU 112 to allow the system to present sounds of words defining patient data, effect warning conditions or other communication with respect to the operator of the system. Speech synthesizer 142 provides electrical output signals which are amplified in an amplifier 143 and converted to analog speech signals by a loud speaker 61.

It is assumed that suitable power supply means is provided on the correct sides of all electronic components and subsystems of the apparatus described herein to properly perform the computing and control functions described.

I claim:

1. A method for detecting tumors and the like existing within living matter, said method comprising:
    (a) producing a quantity of drug units, each containing a quantity of normally inactive nuclide material and an antibody targeted to a selected antigen which defines a structure of a specific tumorous growth existing within a living being,
    (b) administering a dose of said drug units to said living being and allowing a substantial quantity thereof to be targeted to said tumorous growth,
    (c) directing a beam of activating radiation generated exterior of the body of said living being and causing said activiting radiation to scan a portion of said body which contains said tumorous growth so as to intersect the nuclide material of the drug units targeted at the site of said tumorous growth and to cause said nuclide material to become radioactive, whereby such radioactivity serves to destroy at least a portion of said tumorous growth, and
    (d) simultaneously as said nuclide material becomes radioactive and emits radiation, detecting such radiation with a radiation sensing means and causing said sensing means to generate electrical signals which are modulated with information defining the location and concentration of said drug units, and
    (e) applying said modulated electrical signals to control a visual presentation means for generating a visual image of the tumorous growth which is indicated by the radiation generated by said radioactive nuclude material at said site.

2. A method in accordance with claim 1 wherein
    said electrical signals are modulated with image information defining at least some of the destructive effects of said radioactivity generated when the nuclide material of said drug units which are targeted to said growth becomes radioactive, and
    employing said electrical signals to generate a visual indication of the destructive effects of said radiation on a visual presentation means.

3. A method in accordance with claim 1 including repeating steps (a) to (e) at least one additional time so as to destroy additional cells of said tumorous growth and to effect the generation of at least one additional visual presentation of the effects of such treatment.

4. A method of treating a cancer located within a living being, said method comprising:
    (a) administering a first quantity of a drug to the body of a living being,
    (b) effecting the destruction of a first portion of cancerous tissue existing at a site within said body by means of said first quantity of said drug, (c) scanning the site of cancerous tissue by generating and modulating radiation at said site with information defining the shape and extent of said cancerous tissue, (d) detecting and modulating radiation with an electrically energized sensing means and generating first electrical signals on the output of said sensing means, (e) computer processing and analyzing said first electrical signals and generating control signals, and (f) applying said control signals to control a means for controllably administering a further quantity of said drug to the body of said living being and causing said further quantity of said drug to destroy additional cancerous tissue at said site.

5. A method in accordance with claim 4 wherein the radiation generated at said site is created by incorporating anuclide material in said drug and activating said nuclide material at said site of cancerous tissue to cause said nuclide material to generate radiation at said site, which radiation is effective in destroying cells of said cancerous tissue at said site.

6. A method in accordance with claim 5 further including
subjecting the nuclide material of said drug, when it is located at said site, to activating atomic radiation generated as a beam of neutrons and passed through the body of said living being, and causing said nuclide material to become explosively radioactive in a manner to destroy cancerous cells at said site.

7. A method for treating a disease of a living being, which includes:
(a) producing a multitude of drug units, each composed of a monoclonal antibody targeted to a select diseased cell and containing a normally non-radioactive nuclide material capable of being rendered radioactive when exposed to suitable radiation,
(b) administering a select first quantity of said drug units to the body of a living being and allowing the monoclonal antibodies of a portion of such drug units to target the drug units to at least one site of the body of the living being and to become disposed adjacent respective antigens defining diseased cells at said site,
(c) causing the nuclide material of at least certain of said drug units to generate first low intensity detectable radiation by activating the nuclide material of the drug units at said body site with externally generated first activating radiation passed into the body of said living being from an external source of activating radiation,
(d) sensing said first detectable radiation with a first detection means and transducing same to first electrical signals,
(e) computer processing and analyzing said first electrical signals and generating image data relating to the physical characteristics of body matter at the site in the body of said living being to which said drug units have been targeted,
(f) generating first control signals as a result of such analysis and processing and analyzing said first control signals to determine the extent and the location of the disease at said site, and
(g) generating further control signals and applying said further control signals to automatically control the operation of a radiation beam generator in accordance with the information defined by said first control signals to cause said radiation beam generator to generate and direct radiation from a location exterior of said living being through the body of said living being to cause nuclide material of the drug units at said body site to become radioactive to a degree sufficient to radioactively treat said disease at said body site.

8. A method in accordance with claim 7 wherein
step (c) is effected by generating and directing first activating radiation to radioactively activate the nuclide material of the drug units targeted to said site to generate a first level of detection radiation, and
the radiation directed at said site in step (d) is operable to radioactively activate the nuclide material of at least certain of the drug units targeted at said site to a higher level of radiation than the first level of detection radiation, and
said higher level of radiation generated is operable to destroy tissue cells, such as cancer cells, at said site.

9. A method in accordance with claim 8 wherein
step (g) is effected by generating a beam of neutrons externally of the body of said living being and directing said neutrons along a path to intersect said one site at which said drug units are targeted.

10. A method in accordance with claim 7 wherein
steps (c) and (g) are effected by generating respective amounts of activating radiation externally of the body of said living being, each respective amount at a different level of radiation intensity so that one of the radiation levels is higher than the other, and
directing said activating radiation through the living being's body to intersect the nuclide material of said drug units,
the higher level of radiation being operable to cause the nuclide material of said drug units to be rendered radioactive and generate a higher level of radioactivity than that generated by the nuclide material of said drug units when said first activating radiation is directed thereat.

11. A method in accordance with claim 10 which includes
effecting relative scanning movement between said radiation generated externally of said living being and the body of said living being in a manner to cause said radiation to scan selected portions of the living being's body other than the portion thereof containing said site, and
directing radiation generated by the nuclide material of the drug units disposed within the body of said living being in a manner to locate said site from the exterior of the living being' body.

12. A method in accordance with claim 11 wherein
the external radiation passed through the body of said living being is operable to effect the generation of said detectable radiation generated by nuclide material located within the living being's body, and
the radiation defined in step (g) comprises different intensities of the same type of activating radiation.

13. A method in accordance with claim 12 wherein
said externally generated nuclide activating radiation is neutron radiation generated by a neutron beam generator.

14. A method in accordance with claim 7 wherein
step (c) is effected by generating a first type of atomic radiation externally of the body of said living being, thereafter receiving low intensity detection radiation generated when said first atomic radiation activates nuclide material at said site with a detection means, and effecting the scanning of at least a portion of said living being's body to locate said site by detecting and analyzing the concentration of said first low intensity detectable radiation emitted by the nuclide material at said site.

15. A method in accordance with claim 14 including operating said radiation beam generator to cause it to generate radiation which is greater in intensity than that radiation which is generated to cause the generation of detectable radiation in step (c).

16. A method in accordance with claim 8 wherein said higher level of radiation, generated by activation of the nuclide material at said site by activating radiation generated by said automatically operated radiation beam generator, is operable to treat and change the physical condition of living cells defined by antigens to which said antibodies of said drug units are targeted.

17. A method in accordance with claim 9 wherein said higher level of radiation generated at said site by the activation of said nuclide material thereat is of sufficient intensity to destroy tissue cells in the vicinity of the drug units targeted to the antigens at said site.

18. A method in accordance with claim 9 wherein said higher level of radiation is atomically explosive and operable to generate high velocity particles which are capable of penetrating and destroying tissue cells in the immediate vicinity of said drug units located at said site.

19. A method in accordance with claim 8 wherein control of said radiation beam generator in step (g) is effected by generating said first control signals as a result of computer processing and analyzing the electrical signals generated in step (d).

20. A method in accordance with claim 7 wherein said control of said radiation beam generator in step (g) is automatically effected by control signals generated as a result of the computer analysis of the electrical signals generated in step (d).

21. A method in accordance with claim 7 wherein cancer cells are located at said one site and are destroyed by means of the radioactivity of the nuclide generated when such nuclide is activated with radiation of said radiation beam generator directed at said site.

22. A method for treating a malady existing in a living being, which method includes the steps of:

(a) disposing a plurality of drug units, each containing normally inactive nuclide material, (b) concentrating said drug units at a select site in a living being, at which site is located a quantity of diseased tissue, (c) causing nuclide material of said drug units to become radioactive by directing activating radiation through the body of said living being to the site of said concentration of said drug units to activate said nuclide material to cause it to generate first detectable radiation at said site, (d) sensing said detectable radiation with an electronic detection means and generating electrical signals, (e) processing said electrical signals and determining the location of said site and the concentration of nuclide material at said site, and (f) when it is determined that a predetermined concentration of nuclide material exists at said site, further activating nuclide material at said site to produce an increase in the level of radiation generated at an intensity sufficient to destroy at least a portion of the diseased tissue at said site.

23. A method in accordance with claim 22 which includes electrically detecting said latter radiation and generating further electrical signals, computer processing and analyzing said further electrical signals and utilizing same to intelligibly indicate the extent of the destruction of the diseased tissue by said latter radiation.

24. A method in accordance with claim 22 which includes sensing said latter radiation while it is active in destroying tissue and generating further electrical signals, computer processing and analyzing said further electrical signals and generating further control signals, and employing said further control signals to control a visual indicating means to visually indicate the destructive effects of said latter radiation on the diseased tissue at said site.

25. A method of treating cancer in a living being, said method comprising:

(a) administering a plurality of drug units to the body of a living being having cancer cells, (b) each of said drug units includes an antibody targeted to antigens of the cancer cells and a normally non-radioactive nuclide material capable of being rendered radioactive by radiation generated externally of the living being's body and directed at said drug units, (c) detecting at least one concentration of said drug units by activating the nuclide material thereof with atomic radiation generated exterior of the body of said living being after said concentration of drug units has become targeted to a specific cancer site in said living being and causing said activated nuclide material to generate detectable radiation, then (d) sensing said detectable radiation with a sensing means disposed exterior of said body to determine the location of said cancer site, and (e) upon determining the location of said cancer site, directing a beam of neutron radiation at such site by generating such neutron radiation externally of said body and passing said neutron radiation through said body as a beam of neutrons directed at said site to cause neutrons of said beam to intersect the nuclide material of said drug units at said site and to cause said nuclide material to become explosively radioactive in a manner to destroy respective of the cancer cells to which said drug units are targeted at said site.

26. A method in accordance with claim 25 wherein the step of detecting said concentration of drug units is effected by causing the material of said drug units at said cancer site to generate detectable radiation by activating radiation directed through said body to said site from the exterior of the body of said living being and sensing said detectable radiation with a plurality of sensors located outside of the body.

27. A method in accordance with claim 26 wherein the detection of said concentration of said drug units at said site is effected by causing said nuclide material in said drug units to become radioactive after such units become targeted to cancer cells located at said site to generate and direct detectable radiation through the body, and electronically detecting said detectable radiation and generating electrical signals which vary in accordance with the intensity of said detectable radiation generated, and
employing said electrical signals to effect the generation of an image of the site of said drug units, which image is capable of being analyzed to determine the extent of said cancer.

28. A method in accordance with claim 27 wherein said normally inactive nuclide material is activated by neutron radiation, and
the concentration of radiation generated by said nuclide material, when so activated, is detected to provide an indication of the density and distribution of cancer cells at said site in said living being.

29. A method in accordance with claim 25 wherein at least a portion of the nuclide material contained in said drug units is caused to atomically disintegrate when activated by said neutron radiation passed through the body of said living being and generates high velocity particles which penetrate and destroy a multitude of cancer cells at said site to which said drug units are targeted.

30. A method in accordance with claim 25 wherein the detection of said concentration of said drug units is effected at least in part by X-radiation passed through the body of said living being including the site of said cancer,
said X-radiation is detected and employed to generate an image of said site, and
the nuclide material of the drug units targeted to said site is activated to generate additional radiation,
said method including forming a viewable image by electrical signals generated by sensing X-radiation which is modulated in passing through the body of said living being and the radiation generated by said nuclide material when it is rendered radioactive at said site.

31. A method in accordance with claim 25 including applying at least one pulse of magnetic field energy to the body of said living being to cause matter in tissue cells of said living being in the vicinity of said site to undergo magnetic spin resonance, and
effecting a computerized axial tomographic scan of a portion of said body containing said site,
further forming a computer constructed image of said site with the information derived from said tomographic scan to display the extent and configuration of cancer at said site.

32. A method in accordance with claim 25 including administering additional quantities of said drug units containing said nuclide material to said living being,
allowing the drug units of each of said administered quantities to target to respective cancer cells, and
generating and directing said beam of activating radiation through said body to said site each time a quantity of said drug units becomes targeted to cancer cells at said site to cause nuclide material of each quantity of said drug units at said site to become radioactive and destroy additional cancer cells at said site.

33. A method of treating a tumor, said method comprising:
(a) disposing a first select quantity of a normally inactive nuclide material adjacent the tumor in a body of a living being and thereafter causing said nuclide material to become radioactive in a manner to destroy a first group of tumor cells,
(b) detecting and intelligibly indicating the extent of damage to said first group of tumor cells caused by the radioactivity of the nuclide material rendered radioactive adjacent said tumor,
(c) thereafter disposing a second select quantity of normally inactive nuclide material adjacent a portion of the tumor which remains, and
(d) causing said second quantity of nuclide material to become radioactive in the vicinity of said tumor,
(e) detecting and determining the extent of cell damage to the remaining cells of said tumor and repeating the above steps as many times as necessary to destroy the tumor.

34. A method in accordance with claim 33 wherein said first and second select quantities of said nuclide material are disposed in the body of the living being containing said tumor by controllably injecting said quantities of drug units targeted to the cells of said tumor into the blood circulatory system of said living being.

35. A method in accordance with claim 33 wherein said select quantities of cell destroying nuclide material are disposed adjacent respective cells of said tumor by attaching respective quantities of said nuclide material to respective antibodies targeted to the cells of the tumor to be destroyed.

36. A method in accordance with claim 33 which includes
periodically administering select amounts of drug units,
each drug unit formed of a respective nuclide material and a respective antibody targeted to antigenic matter of the tumor to be destroyed after it has been partly destroyed and detecting the concentration of said drug units at the site of said tumor to indicate the presence of remaining concentrations of the cancer cells in said body.

37. A method in accordance with claim 36, wherein the step of causing said nuclide material of said drug units to become radioactive at the site of said tumor is automatically controlled by a computer analyzing electrical signals generated by sensing means operable to sense radiation which is modulated with information defining tissue cell formations at the tumor site to generate control signals, and
said control signals are applied to control and direct nuclide activating radiation towards said site to cause said radiation to intersect and cause the nuclide material of said drug units to become radioactive.

38. A method for treating a disease of a living being, said method comprising:
(a) producing a multitude of drug units, each composed of a monoclonal antibody targeted to a select disease cell and a normally inactive nuclide material capable of being rendered radioactive when exposed to external radiation,
(b) administering a select quantity of said drug units to a living being and allowing a portion of such units to target to at least one site in such living being's body wherein the antibodies of said drug units become attached to respective antigens defining diseased cells at said site, (c) detecting the location of said site in said living being's body to which such antibodies are targeted by generating first, low intensity detectable radiation, (d) passing said first radiation through tissue in said site and sensing said first detectable radiation with a first detector means, (e) generating analog electrical signals on the output of said first detection means, (f) computer processing and analyzing the analog electrical signals and generating an image of said site within the body, (g) generating control signals as a result of such computer analysis, and (h) automatically operating an image generating means to cause said generating means to generate an image of said site for use in diagnosing and treating such tissue.

39. A method in accordance with claim 1 wherein the antibody is a monoclonal antibody.

* * * * *